United States Patent [19]

Gambs

[11] 3,982,827

[45] Sept. 28, 1976

[54] OPTHALMIC INSTRUMENT

[76] Inventor: Paul Frédéric Marie Gambs, Chemin du Petit Bois, Ecully (Rhone), France

[22] Filed: Mar. 18, 1975

[21] Appl. No.: 559,419

[30] Foreign Application Priority Data

Mar. 20, 1974 France .............................. 74.10418

[52] U.S. Cl. ................................ 351/14; 240/4.2; 350/292; 350/299; 351/16
[51] Int. Cl.² ........................ A61B 3/10; G02B 5/08
[58] Field of Search ......................... 351/14, 15, 16; 350/292, 299; 240/4.2

[56] References Cited
UNITED STATES PATENTS 3,533,685  10/1970  Littmann et al. ...................... 351/14

Primary Examiner—Paul A. Sacher
Attorney, Agent, or Firm—Karl F. Ross; Herbert Dubno

[57] ABSTRACT

An opthalmic biomicroscope for observing a narrow zone of a patient's eye has an optical axis traversing one of several sections of a flat semitransparent mirror serving to illuminate that zone with the projected image of a slit diaphragm in the ray path of a light source. The light source and the associated diaphragm and projection system are disposed in a housing which is swingable about a pivotal axis skew to the optical axis of the microscope so as to train a high-intensity beam upon the eye by way of a selected mirror section. These sections are relatively inclined in a plane perpendicular to the pivotal axis, including the optical axis of the microscope, and are tangent in that plane to an ellipse whose foci lie on the pivotal axis and on the projected slit image.

6 Claims, 2 Drawing Figures

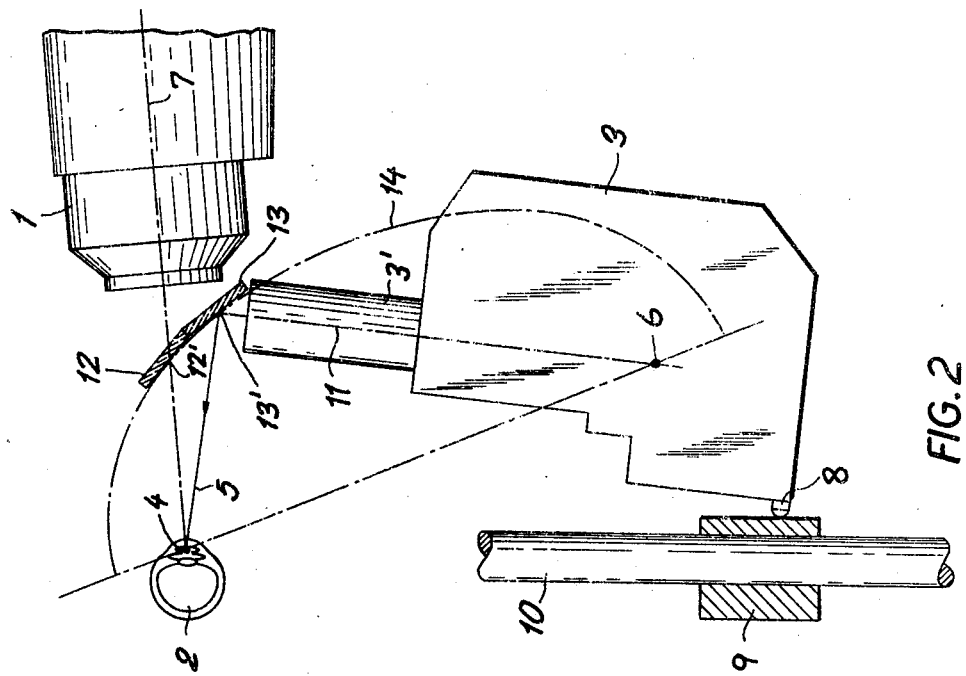
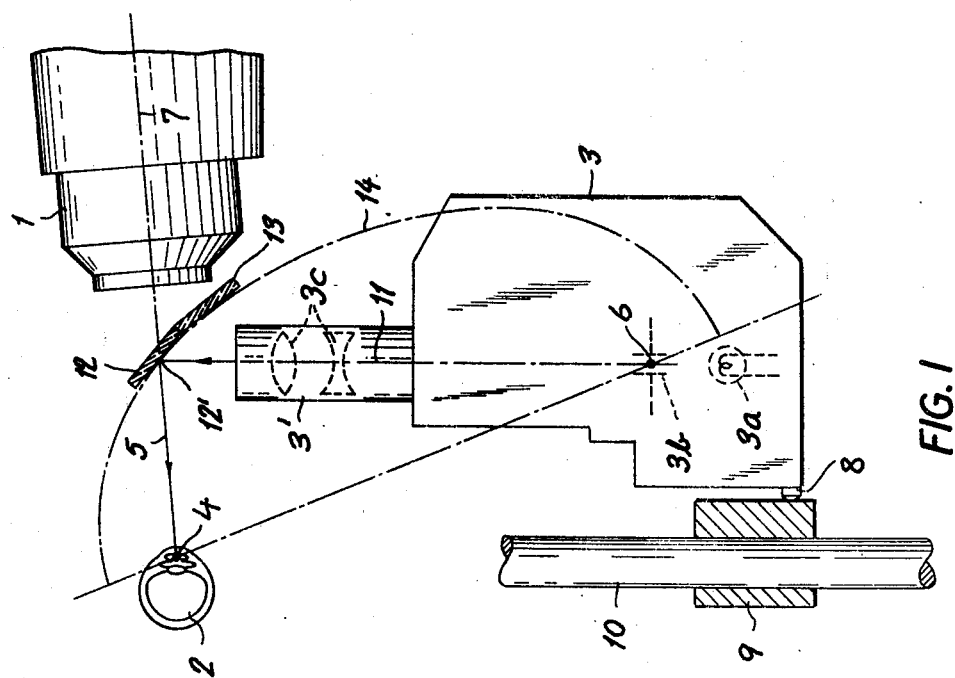

OPTHALMIC INSTRUMENT

FIELD OF THE INVENTION

My present invention relates to an ophthalmic instrument including a biomicroscope for observing a narrow zone of a patient's eye that is being illuminated by a beam of light passing into the eye along a line which may or may not coincide with the optical axis of the biomicroscope.

BACKGROUND OF THE INVENTION

It is known, e.g. from French patents Nos. 1,195,279 and 1,307,410, to provide the light source with a slit diaphragm and with a projector which images that slit on a predetermined point in line with the optical axis of the microscope, namely a point located during examination in the zone of the patient's eye that is to be observed. By a pivotal movement of the projector, trained upon a mirror, the angle of incidence of the beam upon the zone of observation can be varied.

In these known instruments it is necessary to take into consideration, regarding the location of the pivotal axis, both the mechanical requirements and the optical conditions to be satisfied; compromise solutions adopted in the past tend to complicate the system. Moreover, with the pivotal axis and the projector disposed at opposite sides of the mirror, the necessary mounting elements unavoidably obstruct part of the field of view.

OBJECT OF THE INVENTION

The object of my present invention, therefore, is to provide an improved ophthalmic instrument of the character referred to in which these inconveniences are avoided.

SUMMARY OF THE INVENTION

I realize this object, in accordance with my present invention, by the replacement of the single mirror of the conventional system with a plurality of flat, closely juxtaposed mirror sections including different angles with the optical axis of the biomicroscope in a swing plane which is transverse to the pivotal axis of the light source, the latter axis being skew to the optical axis.

According to a more particular feature of my invention, each of the several mirror sections is tangent to an ellipse lying in the transverse swing plane, this ellipse having a first focus on the pivotal axis and a second focus coinciding with the observation point.

If the pivotal axis is substantially horizontal, as will usually be the case, the mounting for the light source may be unbalanced so as to tend to swing unidirectionally about that axis. With the aid of suitable abutment means, such as a stepped eccentric, the mounting of the light source can be arrested in different angular positions in which its beam is trained upon a selected mirror section, in particular upon the point of tangency of that section to the aforedescribed ellipse.

BRIEF DESCRIPTION OF THE DRAWING

The above and other features of my invention will now be described in detail with reference to the accompanying drawing in which:

FIG. 1 is a side-elevational view, somewhat diagrammatic and partly in section, of an ophthalmic instrument embodying my invention; and FIG. 2 is a view similar to FIG. 1, showing a different operating position.

SPECIFIC DESCRIPTION

The instrument shown in the drawing comprises a biomicroscope 1 with an optical axis 7 trained upon the eye 2 of a patient to be examined, more particularly upon an observation point 4 near its pupil. Axis 7 passes through a semitransparent mirror section 12 which is one of several such sections angularly adjoining one another, only one other section 13 having been illustrated. With the arrangement here described, section 13 need not be semitransparent since it does not intersect the microscope axis.

A source of light, designed to illuminate a narrow zone around observation point 4, comprises a mounting 3 which is swingable about a horizontal pivotal axis 6 skew to the optical axis 7. Mounting 3 houses a lamp 3a some of whose rays pass through a diaphragm 3b having a slit in line with axis 6. These rays are focused by a projection objective 3c within an extension 3' of mounting 3 into a beam 5 impinging upon one of the mirror sections 12, 13 which deflects that beam toward the eye 2 so as to image the diaphragm slit upon the observation zone around point 4 whereby this part of the eye is intensely illuminated.

The axis 11 of the incident beam defines with the microscope axis 7 a swing plane, perpendicular to pivotal axis 6, in which an ellipse 14 is defined by a first focus on axis 6 and a second focus on point 4. Mirror sections 12 and 13 are tangent at their midpoints 12', 13' to this imaginary ellipse which may be considered a section of either an ellipsoid of revolution or an elliptical cylinder.

In the position of FIG. 1, beam axis 11 is trained upon point 12' so that the reflected beam 5 coincides with optical axis 7 and the angle of incidence of this beam is zero. In the alternate position of FIG. 2, beam axis 11 strikes the mirror section 13 at point 13' whereby the reflected beam 5 includes an acute angle with optical axis 7.

It will be apparent that the angle of incidence is not affected by the position of diaphragm 3b along line 11 and that a deviation of the diaphragm position from its illustrated alignment with pivotal axis 6 will result only in minor differences between the lengths of the ray paths in the angular positions of FIGS. 1 and 2 so that illumination will be satisfactory in both instances. If the diaphragm slit coincides with axis 6, as shown, it will be sharply imaged at point 4 in the positions of both FIG. 1 and FIG. 2.

The mounting 3 is sufficiently unbalanced to gravitate in a clockwise direction so that a stop 8 thereon will come to bear upon an adjustable abutment 9 in the form of a peripherally stepped cylinder eccentrically mounted on a generally vertical shaft 10. By rotating the cylinder 9 about the shaft, I can selectively tilt the mounting 3 and its optical elements into either of the two angular positions shown in FIGS. 1 and 2. The number of such positions, of course, will have to be increased if more than two mirror sections are provided.

I claim:
1. An ophthalmic instrument comprising:
   a biomicroscope having an optical axis trainable upon a selected zone of a patient's eye;

a light source forming a narrow beam for illuminating said zone, said source being swingable about a pivotal axis skew to said optical axis; and a plurality of flat mirror sections closely juxtaposed with one another and including different angles with said optical axis in a swing plane transverse to said pivotal axis for reflecting said beam from different directions upon a predetermined observation point in line with said optical axis, each of said sections being tangent to an ellipse in said swing plane having a first focus on said pivotal axis and a second focus coinciding with said observation point.

2. An ophthalmic instrument as defined in claim 1 wherein said light source includes a diaphragm with a slit transverse to said swing plane and projection means for forming an image of said slit at said observation point.

3. An ophthalmic instrument as defined in claim 2 wherein said slit substantially registers with said pivotal axis.

4. An ophthalmic instrument as defined in claim 1 wherein at least one of said mirror sections is semi-transparent and intersects said optical axis.

5. An ophthalmic instrument as defined in claim 1 wherein said pivotal axis is substantially horizontal.

6. An ophthalmic instrument as defined in claim 5 wherein said light source has an unbalanced mounting tending to swing unidirectionally about said pivotal axis, further comprising stepped abutment means for arresting said mounting in different angular positions wherein said beam is trained upon different mirror sections.

* * * * *